United States Patent
Khavinson

(10) Patent No.: US 7,101,854 B2
(45) Date of Patent: Sep. 5, 2006

(54) TETRAPEPTIDE STIMULATING THE FUNCTIONAL ACTIVITY OF HEPATOCYTES, PHARMACOLOGICAL SUBSTANCE ON ITS BASIS AND THE METHOD OF ITS APPLICATION

(75) Inventor: Vladimir Khatskelevich Khavinson, St. Petersburg (RU)

(73) Assignee: Sankt-Peterburgskaya Obschestvennaya Organizatsiya "Sankt-Peterburgsky Institut Bioregulyatsii i Gerontologii SZO RAMN", St. Petersburg (RU)

( * ) Notice: Subject to any disclaimer, the term of this patent is extended or adjusted under 35 U.S.C. 154(b) by 459 days.

(21) Appl. No.: 10/398,690

(22) PCT Filed: May 15, 2001

(86) PCT No.: PCT/RU01/00199

§ 371 (c)(1),
(2), (4) Date: Apr. 8, 2003

(87) PCT Pub. No.: WO02/30955

PCT Pub. Date: Apr. 18, 2002

(65) Prior Publication Data

US 2004/0009925 A1    Jan. 15, 2004

(30) Foreign Application Priority Data

Oct. 9, 2000   (RU) .............................. 2001125353

(51) Int. Cl.
*A61K 38/06*   (2006.01)
*C07K 5/06*   (2006.01)

(52) U.S. Cl. ........................................ 514/18; 530/330
(58) Field of Classification Search .................. 514/2, 514/18; 530/330
See application file for complete search history.

(56) References Cited

OTHER PUBLICATIONS

H. Sponsel et al., "Mechanisms of Recovery from Mechanical Injury of Cultured Rat Hepatocytes", *Am. J. Physiol.*, pp. C721-727 (1996).
H. Sponsel et al., "Mechanisms of Recovery From Mechanical Injury of Rental Tubular Epithelial Cells", *Am. J. Physiol.*, 267, pp. F257-F264 (1994).
V. Khavinson, "Tissue—Specific Effects of Peptides", *Exper. Biol. and Med.* 132(2), pp. 807-808 (2001).

*Primary Examiner*—Bruce R. Campell
*Assistant Examiner*—B. Dell Chism
(74) *Attorney, Agent, or Firm*—Leydig, Voit & Mayer, Ltd.

(57) ABSTRACT

The invention refers to the field of medicine and may be applied as a substance stimulating the functional activity of hepatocytes, restoring the synthesis of non-specific proteins, normalising metabolism activating the processes of proliferation and differentiation of the liver cells. There is proposed a new compound -tetrapeptide lysyl-glutamyl-aspartyl-alanine of the general formula Lys-Glu-Asp-Ala [SEQ ID NO:1]. There is proposed a pharmaceutical composition capable of stimulating the functional activity of hepatocytes and a pharmaceutical peptide substance containing as its active base a therapeutically effective quantity of tetrapeptide of the formula Lys-Glu-Asp-Ala [SEQ ID NO:1] or one of its salts intended for parenteral administration. There is proposed a method of stimulating the functional activity of hepatocytes including therapeutic administration to a patient of the pharmaceutical peptide substance in doses 0.01–100 μg/kg of the body weight at least once a day during a period required for attaining a therapeutic effect.

11 Claims, 3 Drawing Sheets

Figure 2:
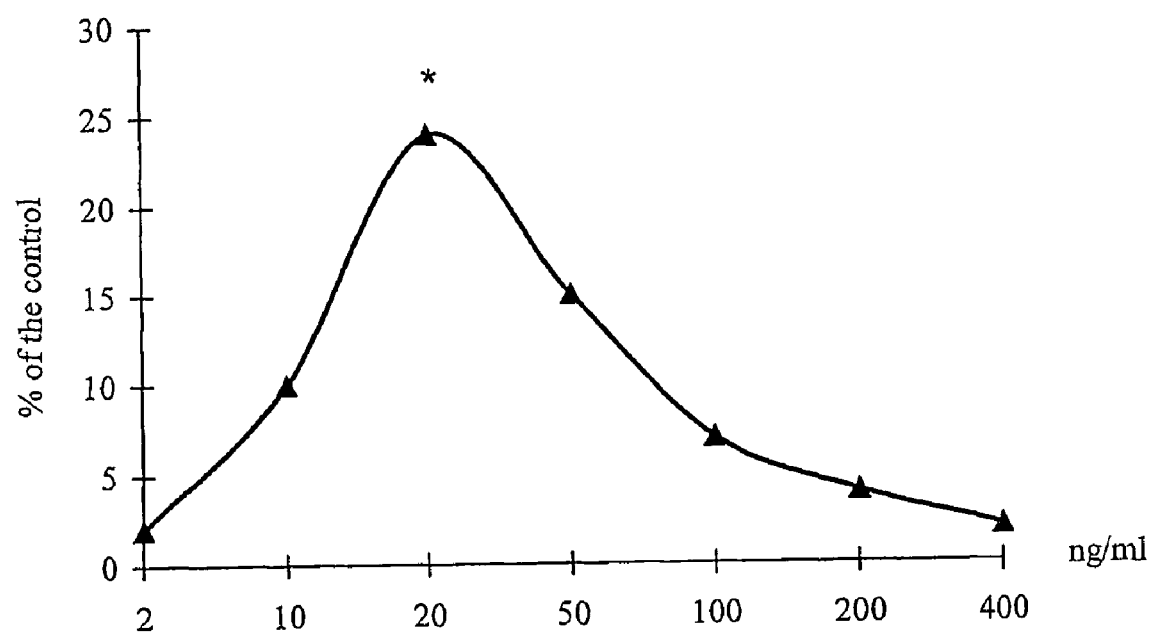

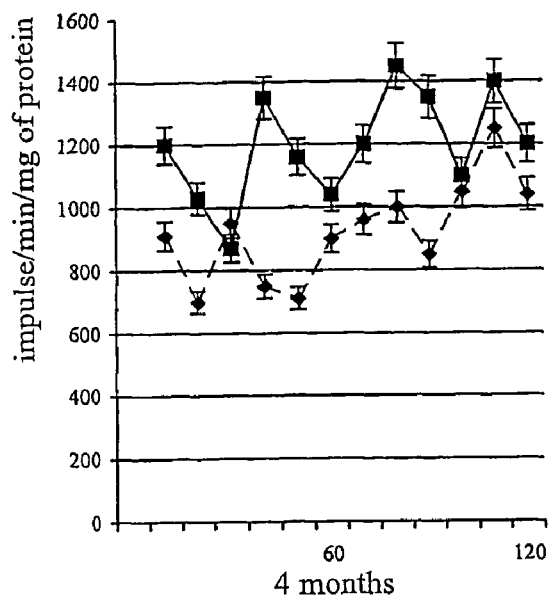
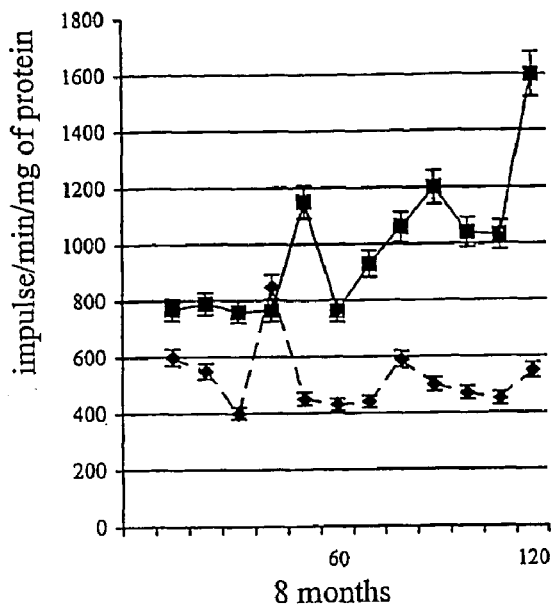
Figure 1a
Figure 1b
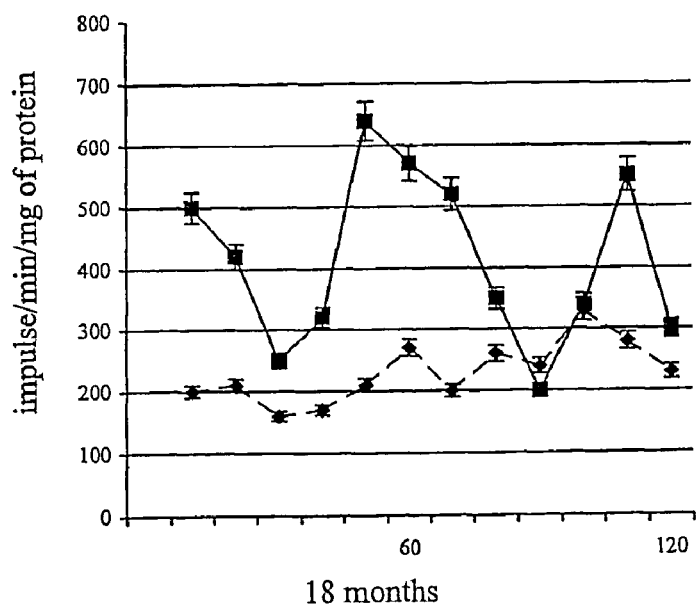
Figure 1c

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Tetrapeptide Lys Glu Asp Ala stimulates the
      functional activity of hepatocytes by restoring the synthesis of
      tissue-specific proteins

<400> SEQUENCE: 1

Lys Glu Asp Ala
1

TETRAPEPTIDE STIMULATING THE FUNCTIONAL ACTIVITY OF HEPATOCYTES, PHARMACOLOGICAL SUBSTANCE ON ITS BASIS AND THE METHOD OF ITS APPLICATION

The invention refers to the field of medicine and may be applied as a substance stimulating the functional activity of hepatocytes in prevention of and treatment for liver diseases and lesions.

Among the closest application analogues of this substance there is known a group of hepatoprotective substances improving metabolic processes in the liver, enhancing its resistance to pathogenic impacts and accelerating its functional recovery after various lesions (1). Nowadays, certain flavonoids (Silibinin, Silibore, Cathergen) structurally close to Group P vitamins (Rutin, Quartzetin) and preparations of medical herbs (Liv-52, Valilive, etc.) are employed as special hepatoprotectors. Their action is mainly associated with increased activity of the liver ferment systems, general antioxidative and antihypotoxic activity. Administration of these medications may result in dyspeptic phenomena and individual intolerance. Some of these preparations are prohibited in case of severe lesions of parenchymal organs, acute inflammatory processes in gall and urinary tracts.

There is known to the general public Essentiale (2), a complex pharmaceutical, applied in chronic liver diseases and lesions. The drug diminishes jaundice, improves ferment process development, biochemical indices and microcirculation. However, application of Essentiale does not provide any therapeutic effect in case of acute liver lesions.

There is known pharmaceutical Syrepar (3), a liver hydrolysate. Syrepar promotes restoration of the liver parenchyma, prevents adipose infiltration and affects the synthesis of choline and methionine. It is applied in subacute and chronic hepatitis, adipose liver degeneration of various aetiologies, toxically and pharmaceutically entailed lesions of the liver parenchyma and in liver cirrhosis. Nevertheless, Syrepar is potentially allergenic and its therapeutic effect is weak.

Shortcoming of the above-adduced agents is also their poorly expressed specific regulatory influence upon the functional activity of hepatocytes.

There is known a hepatocyte growth factor synthesised by the liver cells. Introduction of the hepatocyte growth factor into a culture of isolated hepatocytes accelerated intracellular DNA synthesis (4). Application of the hepatocyte growth factor in rats with legated branches of the liver portal vein increased DNA synthesis in the cells of non-blocked liver lobes and curbed bilirubin level in jaundice-affected rats (5). Raised level of the endogenous hepatocyte growth factor in the blood plasma of rats with experimental hepatocirrhosis slowed the process of fibrous tissue formation and inhibited hepatocytic apoptosis (6).

Nonetheless, it has been proven by now that the hepatocyte growth factor can be also synthesised in the epithelial cells of the cornea, keratinocytes and endothelial cells, while receptors to this factor can be found in the cornea cells (7). Therefore, the hepatocyte growth factor stimulates proliferation of the cornea cells and induces their migration, which reflects the lack of significant tissue-specific effect.

Moreover, obtaining of the recombinant hepatocyte growth factor is associated with certain technological difficulties impeding its adoption in clinical practice.

The proposed invention is designed to obtain a new biologically active compound of peptide nature stimulating the functional activity of hepatocytes.

The proposed peptide compound is a tetrapeptide having no structural analogues.

In this patent claim there is described tetrapeptide lysyl-glutamyl-aspartyl-alanine of the general formula Lys-Glu-Asp-Ala (SEQ ID NO: 1).

In this patent claim there is described tetrapeptide lysyl-glutamyl-aspartyl-alanine of the following amino acid sequence: Lys-Glu-Asp-Ala (SEQ ID NO: 1), revealing biological activity, which consists in stimulating the functional activity of hepatocytes by restoring the synthesis of tissue-specific proteins, normalising metabolism, activating proliferation processes and hepatocyte differentiation.

The tetrapeptide is obtained by a classical method of peptide synthesis in a solution (8).

The stimulating effect of tetrapeptide Lys-Glu-Asp-Ala (SEQ ID NO: 1) on the functional activity of hepatocytes has been revealed experimentally. The tetrapeptide biological activity has been studied in a monolayer hepatocyte culture, in liver explants—to investigate its tissue-specificity and in rats—to study the liver structural-functional indices in case of toxically entailed lesions and tumour growth.

In this patent claim there is described a pharmaceutical peptide substance revealing a hepatoprotective activity and containing as its active base a therapeutically effective quantity of tetrapeptide of the formula lysyl-glutamyl-aspartyl-alanine (Lys-Glu-Asp-Ala) (SEQ ID NO: 1) or one of its pharmaceutically admissible salts and a pharmaceutically admissible carrier.

This patent claim describes a pharmaceutical peptide substance stimulating the functional activity of hepatocytes, which can contain one of its salts of the amino acid group (acetate, hydrochloride, oxalate) or carboxyl groups (salts of metals—sodium, potassium, calcium, lithium, zinc, magnesium, as well as of other organic and inorganic cations—ammonium and triethylammonium).

The patent claim describes a pharmaceutical peptide substance intended for parenteral administration as a sole medication for preventive and/or therapeutic application or in combination with other pharmaceuticals.

The proposed pharmaceutical peptide substance stimulating the functional activity of hepatocytes is capable of restoring the metabolism and repair ability of damaged liver structures.

The notion "pharmaceutical peptide substance" under this patent claim implies the use of any drug form containing as its active base the tetrapeptide or one of its salts, which can find its preventive and/or therapeutic employment in medicine as an agent restoring the structural-functional integrity of the liver tissue.

The notion "therapeutically effective quantity" under this application implies the use of such an amount of the active base, which, in compliance with the quantitative indices of its activity and toxicity, as well as with respect to the knowledge available, shall be effective in a given drug form.

The notion "pharmaceutical composition" under this patent claim implies application of the tetrapeptide in the form of solution.

To obtain pharmaceutical compositions meeting the invention, the proposed tetrapeptide or its salts are blended as an active base and a pharmaceutically admissible carrier in accordance with the methods of compounding accepted in pharmaceutics.

The carrier for parenteral administration usually includes sterile water, though there could be employed other ingredients instrumental for stability or maintaining sterility.

The patent claim describes a method of treating for liver diseases and pathologic states embracing preventive or therapeutic administration to a patient of the proposed pharmaceutical peptide substance in doses 0.01–100 μg/kg of the body weight at least once a day during a period required for attaining a therapeutic effect, i.e. 10–40 days with respect to the character and severity of the treated pathologic process.

The proposed tetrapeptide is active when introduced in doses 0.01–100 μg/kg of the body weight, though low/higher doses are admissible depending on the character and severity of the treated pathologic process.

The invention is illustrated by an example of synthesis of tetrapeptide lysyl-glutamyl-aspartyl-alanine (Lys-Glu-Asp-Ala) (SEQ ID NO: 1) (Example 1), examples of testing the tetrapeptide for toxicity and biological activity (Examples 2, 3, 4, 5, 6) and an example of the tetrapeptide clinical application demonstrating its pharmacological properties and confirming the possibility of attaining a preventive and/or therapeutic effect (Example 7).

EXAMPLE 1

Synthesis of Lys-Glu-Asp-Ala (SEQ ID NO: 1) Tetrapeptide

1. Product name: lysyl-glutamyl-aspartyl-alanine.
2. Structural formula: H-Lys-Glu-Asp-Ala-OH (SEQ ID NO: 1)

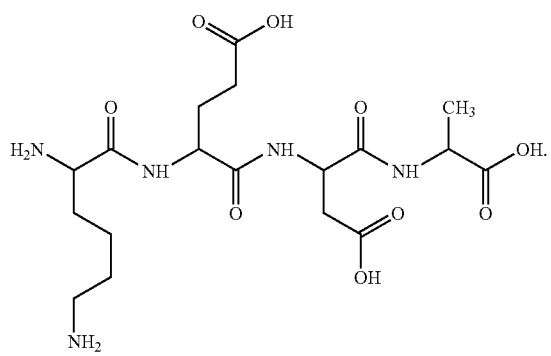

3. Molecular formula without ion pair: $C_{18}H_{31}N_5O_9$.
4. Molecular weight without ion pair: 461.48.
5. Ion pair: acetate.
6. Appearance: white amorphous powder without smell.
7. Method of synthesis: the peptide is obtained by a classical method of synthesis in a solution by the following scheme:

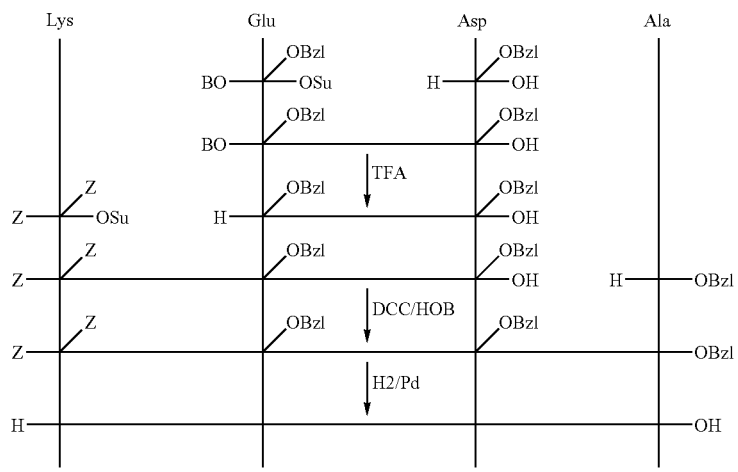

Z -benzyloxycarbonyl group;
BOC -tert.butyloxycarbonyl group;
OSu -N-oxysuccinimide ester;
OBzl -benzyl ester;
DCC -N,N'-dicyclohexylcarbodiimide;
HOBT -N-oxybenzotriazol.

N,N'-dimethylformamide was used as a solvent. When adding aspartic acid, the defence of α-COOH group was applied to salification with triethylamine. BOC-protecting group was removed with trifluoracetic acid (TFA) solution and Z-protecting groups—with catalytic hydrogenation. The product was extracted and purified by the method of preparative high-performance liquid chromatography (HPLC) on a reversed phase column.

Properties of the finished product:

| amino acid analysis | Lys | Glu | Asp | Ala |
|---|---|---|---|---|
| | 0.97 | 1.02 | 1.01 | 1.00 | peptide content 98.75% (by HPLC, 220 nm);
thin layer chromatography (TLC)-individual, $R_f$ = 0.71 (acetonitrile-water 1:1); moisture content: 7%;
pH of 0.001%-solution: 5.54;
specific rotary power: $[α]_D^{23}$:
−28.0° (c = 1.0; $H_2O$), "Polamat A", Carl Zeiβ Jena.

EXAMPLE OF SYNTHESIS

1. BOC-Glu(OBzl)-Asp(OBzl)-OH1(I), N-tert.butyloxycarbonyl-(γ-benzyl)glutamyl-(β-benzyl)aspartate.

4.34 g (0.0100 mole) of N-oxysuccinimide ester of N-tert.butyloxycarbonyl-(γ-benzyl)glutamic acid (BOC-Glu(OBzl)-OSu) is dissolved in 20 ml of dimethylformamide and added 1.72 ml (0.0125 mole) of triethylamine and 2.80 g (0.0125 mole) of β-benzylaspartate. The mixture is stirred for 24 hours at room temperature. Afterwards the product is precipitated with 0.5N sulphuric acid solution (150 ml), extracted by ethyl acetate (3×30 ml), washed in 0.5N sulphuric acid solution (2×20 ml), water, 5% solution of sodium bicarbonate (1×20 ml), water, 0.5N sulphuric acid solution (2×20 ml), water. The product is dried over anhydrous $Na_2SO_4$. Ethyl acetate is filtered and removed in vacuo at 40° C., the residue is dried in vacuo over $P_2O_5$. 5.68 g (≈100%) of oil is obtained. $R_f$=0.42 (benzene-acetone 2:1, Sorbfil plates, Silicagel-8–12 μm, development by UV and chlorine/benzidine).

2. TFA.H-Glu(OBzl)-Asp(OBzl)-OH (II), (γ-benzyl)glutamyl-(β-benzyl) aspartate trifluoracetate.

5.68 g (≈0.01 mole) of N-tert.butyloxycarbonyl-(γ-benzyl)glutamyl-(β-benzyl)aspartate (I) is dissolved in 20 ml of dichlormethan-trifluoracetic acid mixture (3:1). Two hours later the solvent is removed in vacuo at 40° C. The removal is repeated with an addition of another portion of dichlormethan (2×10 ml). The residue is dried in vacuo over NaOH and 5.80 g (≈100%) of oil is obtained. $R_f$=0.63 (n-butanol-pyridine-acetic acid-water, 15:10:3:12).

3. Z-Lys(Z)-Glu(OBzl)-Asp(OBzl)-OH (III), N,N$^ε$-dibenzyloxycarbonyllysyl-(γ-benzyl)glutamyl-(β-benzyl)aspartate.

5.65 g (0.01 mole) of (γ-benzyl)glutamyl-(β-benzyl)aspartate trifluoracetate (II) is dissolved in 10 ml of dimethylformamide, added 2.80 ml (0.02 mole) of triethylamine and 6.64 g (0.013 mole) of N-oxysuccinimide ester of N,N$^ε$-dibenzyloxycarbonyllysine. The reacting mixture is stirred for 24 hours at room temperature.

The product is precipitated with 0.5N sulphuric acid solution (150 ml), extracted by ethyl acetate (3×30 ml), washed in 0.5N sulphuric acid solution (2×20 ml), water, 5% sodium bicarbonate solution (1×20 ml), water, 0.5N sulphuric acid solution (2×20 ml), water and dried over anhydrous $Na_2SO_4$. Ethyl acetate is filtered and removed in vacuo at 40° C. The residue is recrystallised in the ethyl acetate/hexane system. The product is filtered and dried in vacuo over $P_2O_5$. The yield is 6.04 g (72%). The temperature of melting ($T_{ml}$) is 142° C. $R_f$=0.60 (benzene-acetone, 1:1).

4. Z-Lys(Z)-Glu(OBzl)-Asp(OBzl)-Ala-OBzl (IV), N,N$^ε$-dibenzyloxycarbonyllysyl (γ-benzyl)glutamyl-(β-benzyl)aspartyl-alanine benzyl ester.

0.65 g (3 mmole) of alanine benzyl ester chloride (HCl.H-Ala-OBzl) is suspended in 15 ml of tetrahydrofuran and added 0.4 ml (3 mmole) of triethylamine while stirring. In 5 minutes 1.68 g (2 mmole) of N,N$^ε$-dibenzyloxycarbonyllysyl (γ-benzyl)glutamyl-(β-benzyl)aspartate (III) and 0.27 g (2 mmole) of N-oxybenzotriazol are added. The mixture is cooled down to 0° C. Afterwards, 0.42 g (2 mmole) of N,N'-dicyclohexylcarbodiimide solution cooled down to 0° C. is added in 5 ml of tetrahydrofuran. The mixture is stirred at this temperature for 2 hours and left to blend for a night at room temperature. The residue of dicyclohexylurea is filtered out, the solvent is removed in vacuo and the residue is dissolved in 30 ml of ethyl acetate. The solution is washed in 1N sulphuric acid solution, water, 5% sodium bicarbonate solution, water, 1N sulphuric acid solution, water, and dried over anhydrous $Na_2SO_4$. The solvent is removed in vacuo and the product is recrystallised in the ethyl acetate/hexane system. The yield is 1.28 g (64%). $T_{ml}$=156-160° C. $R_f$=0.67 (benzene-acetone, 2:1).

5. H-Lys-Glu-Asp-Ala-OH (SEQ ID NO: 1) (V), lysyl-glutamyl-aspartyl-alanine.

1.1 g of N,N$^ε$-dibenzyloxycarbonyllysyl-(γ-benzyl)glutamyl-(β-benzyl)aspartyl-alanine benzyl ester (III) is hydrogenated in the methanol/water/acetic acid system (3:1:1) over Pd/C catalyst. Completeness of the deblocking reaction is monitored by TLC method in the benzene/acetone (2:1) and acetonitrile/acetic acid/water (5:1:3) systems. At the reaction completion the catalyst is filtered, the filtrate is removed in vacuo and the residue is recrystallised in the water/methanol system. The product is dried in vacuo over KOH. The yield is 0.484 g (95%). $R_f$=0.71 (acetonitrile/water, 1:1).

For purification, 470 mg of the product is dissolved in 4 ml of 0.01%-trifluoracetic acid (sample pH is 2.23) and subjected to HPLC on a reversed phase column (50×250 mm, Diasorb-130-C16T, 7μ). The employed chromatograph is Beckman System Gold, 126 Solvent Module, 168 Diode Array Detector Module. The conditions of chromatography A: 0.1% of TFA; B: 50% of MeCN/0.1% of TFA, gradient B 0→16% per 240 minutes. Sample volume constitutes 5 ml, detection is conducted by 215 nm, scanning—by 190–600 nm. The flow rate equals 10 ml/min. The fraction is selected within 94–135 min.

The solvent is removed in vacuo at a temperature not exceeding 40° C. The removal is multiply repeated (5 times) with 10 ml of 10% acetic acid solution. The residue is ultimately dissolved in 20 ml of deionised water and lyophilised. 255 mg of purified product in the form of amorphous odourless white powder is obtained.

In order to obtain corresponding salts of carboxyl groups, the free tetrapeptide is added a calculated amount of the aqueous solution of a corresponding metal hydroxide (NaOH, KOH, $Zn(OH)_2$, LiOH, $Ca(OH)_2$, $Mg(OH)_2$, $NH_4OH$). To obtain triethylammonium salt, the processing is carried out similarly, triethylamine being used as the base.

6. Analysis of the Finished Product.

Peptide content is defined by HPLC on Supelco LC-18-DB column, 4.6×250 mm, grad. LC-18-DB. A: 0.1% of TFA; B: 50% of MeCN/0.1% of TFA; grad. B 0→20% per 30 min. The flow speed equals 1 ml/min. Detection by 220 nm, scanning—by 190–600 nm, the sample volume is 20 μl. Peptide content—98.75%.

The amino acid analysis is carried out on AAA "T-339" tester, Prague. Hydrolysis is conducted in 6N HCl at 125° C. for 24 hours.

| Lys | Glu | Asp | Ala |
|---|---|---|---|
| 0.97 | 1.02 | 1.01 | 1.00 |

TLC: individual, $R_f = 0.71$ (acetonitrile/water, 5:1:3). Sorbfil plates, 8–12 μm Silicagel, developing in chlorine/benzidine.
Moisture content: 7% (gravimetrically, according to the mass loss by drying, −20 mg at 100° C.).
pH of 0.001%-solution: 5.54 (potentiometrically).
Specific rotary power: $[\alpha]_D^{23}$: −28° (c = 1.0 $H_2O$), "Polamat A", Carl Zeiß Jena.

The pharmaceutical peptide substance in solution form containing the tetrapeptide or its salts as its active base is obtained the following way: the tetrapeptide or its salts obtained by the above-described method is dissolved in 0.9% isotonic sodium chloride solution. One vial contains 1 ml of the tetrapeptide solution in the concentration of 10 μg/ml.

EXAMPLE 2

Study of Lys-Glu-Asp-Ala (SEQ ID NO: 1) Tetrapeptide for Toxicity

The possible toxic effect of Lys-Glu-Asp-Ala (SEQ ID NO: 1) tetrapeptide on the human organism was studied in compliance with "The Rules of Pre-Clinical Assessment of the Safety of Pharmacological Substances" (GPL).

This study was designed to define the tolerable toxic doses of the preparation, assess the degree and character of pathologic alterations in various organs and systems of the organism and reveal the dependence of toxic effects on the dosage and duration of the preparation intake.

Acute toxicity of Lys-Glu-Asp-Ala (SEQ ID NO: 1) tetrapeptide was defined according to Kerber. Examined were 72 white mongrel male mice weighing 20–22 g. The mice were kept in vivarium under standard regimen and fed upon standard rations. They were randomised to six equal groups, 12 mice in each. The animals were once intramuscularly administered with 0.25 ml of the preparation in the doses of 1 mg/kg, 2 mg/kg, 3 mg/kg, 4 mg/kg and 5 mg/kg (several thousand times exceeding the therapeutic dose recommended for clinical trials). The control animals received the same amount of natural saline solution.

In the course of 72 hours and later in 14 days none of the animals died in either of the groups. No alterations in their general state, behaviour, motor activity, hair and skin integument, physiological discharge were registered.

Consequently, Lys-Glu-Asp-Ala (SEQ ID NO: 1) tetrapeptide administered in doses, which several thousand times exceed the therapeutic one recommended for clinical trials, does not entail any acute toxic reactions, thus revealing a wide therapeutic applicability of the preparation.

Subacute toxicity of Lys-Glu-Asp-Ala (SEQ ID NO: 1) tetrapeptide was investigated on 64 white mongrel rats weighing 170–250 g. The animals were intramuscularly injected with the preparation once a day in the doses of 1 μg/kg, 0.3 mg/kg, 3 mg/kg in 0.5 ml of natural saline solution, daily for 90 days. The control animals were administered with natural saline solution in the same amount.

The animals were under daily observation during the whole course of investigation. Their behaviour, food and water consumption, state of hair integument and mucous membranes were noted. The rats were weighed weekly. Before the preparation administration and on the $30^{th}$, $60^{th}$ and $90^{th}$ days thereof the morphological composition and properties of their peripheral blood were examined. Biochemical and coagulological properties of the blood were studied at the experiment completion.

Lys-Glu-Asp-Ala (SEQ ID NO: 1) tetrapeptide obtained according to the proposed method was investigated for chronic toxicity during its long-term administration to rats weighing 170–250 g. The animals were intramuscularly injected with the preparation in the doses of 1 μg/kg, 0.1 mg/kg, 1 mg/kg in 0.5 ml of natural saline solution, daily for 6 months. Their behaviour, food and water consumption, state of hair integument and mucous membranes were noted. The rats were weighed daily during the first three months of the experiment and then once a month. In three months after the administration onset and at the experiment completion, haematological and biochemical investigations were conducted. The functions of the cardiovascular system, liver, pancreas, kidneys and adrenal glands were assessed. At the end of the tetrapeptide administration, part of the animals were subjected to a post mortem examination to assess the state of various segments of their brain and spinal marrow, heart, aorta, lungs, liver, kidneys, endocrine and immune organs.

Assessment of the animals' general state, morphological and biochemical indices of their peripheral blood, morphological state of their intrinsic organs, cardiovascular and respiratory systems, liver and kidney functions revealed no pathologic alterations.

Study of Lys-Glu-Asp-Ala (SEQ ID NO: 1) tetrapeptide for subacute and chronic toxicity demonstrates the lack of any side effects in case of long-term application of the preparation in doses 100–1000 times exceeding the therapeutic one.

EXAMPLE 3

Effect of Lys-Glu-Asp-Ala (SEQ ID NO: 1) Tetrapeptide on the Intensity of Protein Synthesis in a Monolayer Hepatocyte Culture of Rats of Various Ages The intensity of protein synthesis was investigated in a hepatocyte culture of rats aged 4, 8 and 18 months.

To isolate hepatocytes, rat liver was perfused with calcium-free Hanks' solution added 0.5 mM of EDTA and then 0.05% collagenase solution in Medium 199. The cellular suspension was filtered out and centrifuged. The hepatocyte suspension in the concentration of $5 \times 10^5$ was introduced into Petri's dishes, their bottoms surfaced with collagen-covered glass. Applied Medium 199 contained no bovine serum but was added 0.2 mg/ml of albumen and 5 μg/ml of insulin. The dishes with glass-covered bottoms were placed in a thermostat at 37° C., aerated and added $CO_2$. In 2 hours, the glasses with adhered cells were washed and the medium was changed for a similar one. Twenty-four hours later and after washing the cultures, protein synthesis in them was investigated. Within 24 hours monolayer cultures with densely seated hepatocytes were formed in the cellular suspension at the above given concentration.

Protein synthesis was assessed by [$^3$H]-leucin inclusion regarding the standard errors for a free marked leucin pull in the same culture. The molar activity of the applied leucin equalled 150 Ci/mM. Incubation with marked leucin took 10 minutes. After the incubation the cultures containing marked leucin were washed with the medium and treated with cold (4° C.) sulphuric acid for 90 minutes to isolate non-included leucin. The same culture was rinsed with ethyl alcohol, after which proteins were dissolved with hyamine. Radioactivity of the pull of free intracellular leucin and cellular proteins (in hyamine fraction) after adding the corresponding scintillators was measured on a radioactivity counter SL-30.

The intensity of protein synthesis was calculated by the formula:

$$I_{corr} = I_i \times P_{av} / P_i (cpm), \text{ where}$$

$I_{corr}$—inclusion of leucin regarding the standard errors of free leucin pull, $I_i$—measured radioactivity of the proteins for i-culture, $P_{av}$—mean radioactivity of proteins and pull for the cultures studied in this experiment, $P_i$—total radioactivity of proteins and pull of the same culture.

Hepatocyte culture was incubated with Lys-Glu-Asp-Ala (SEQ ID NO: 1) tetrapeptide in the concentration of 0.005 µg/ml during 4 hours.

FIG. 1a,b,c demonstrates the effect of Lys-Glu-Asp-Ala (SEQ ID NO: 1) tetrapeptide on the protein synthesis kinetics in hepatocyte monolayer culture of rats of various ages.

The level of protein synthesis in the hepatocyte cultures was found to decrease with age (FIG. 1a,b,c), Addition of Lys-Glu-Asp-Ala (SEQ ID NO: 1) tetrapeptide to the culture raised the level of protein synthesis in hepatocytes of rats of various ages. Thereby, the strongest effect was observed in the cells of older animals. Besides, the synthesis oscillation amplitude increased significantly in the hepatocytes of older rats, which enabled a conclusion on a raised degree of the cell population activity synchronisation (FIG. 1a,b,c).

EXAMPLE 4

Effect of Lys-Glu-Asp-Ala (SEQ ID NO: 1) Tetrapeptide on the Development of Liver Explants The experiments were carried out in 53 liver fragments of 10–11-days old chicken embryos. Nutrient medium for the explant cultivation consisted of 35% of Eagle's solution, 25% of foetal calf serum, 35% of Hank's solution and 5% of chicken embryonic extract. The mixture is added glucose (0.6%), insulin (0.5 unit/ml), penicillin (100 unit/ml) and glutamine (2 mM). The liver fragments were placed in this medium and cultivated in Petri's dishes in a thermostat at 36.7° C. during 48 hours. Lys-Glu-Asp-Ala (SEQ ID NO: 1) tetrapeptide was added to the experimental medium in the concentrations of 2, 10, 20, 50, 100, 200 and 400 ng/ml. Square index (SI) was taken for a biological activity criterion and calculated as a correlation of the total explant square including the growth zone to the initial square of a liver fragment. The SI values were expressed per cent, the control SI value taken for 100%.

FIG. 2 demonstrates the effect of Lys-Glu-Asp-Ala (SEQ ID NO: 1) tetrapeptide on the development of liver explants.

In 24 hours of cultivation, the explants on a collagen lining were found to lie flat. Proliferating and migrating cells started to move along the explant periphery. By the tetrapeptide concentration of 20 ng/ml on the third day of the cultivation, a significant increase in the explant SI by 24% was observed as compared to the control value (FIG. 2). In case of longer terms of the liver explant cultivation (up to 7 days), an analogous stimulating effect of the tetrapeptide in the same concentration was revealed.

Consequently, Lys-Glu-Asp-Ala (SEQ ID NO: 1) tetrapeptide exerted a tissue-specific effect upon the liver tissue expressed in the explant growth stimulation.

EXAMPLE 5

Effect of Lys-Glu-Asp-Ala (SEQ ID NO: 1) Tetrapeptide of the Course of Acute Toxic Hepatitis in Rats Acute toxic hepatitis was induced to rats by the administration of $CCl_4$ in refined vegetable oil at the ratio of 1:1. Freshly made solution heated to 30–35° C. was introduced into the femoral region at the ratio of 0.5 ml per 100 g of the animal's body weight, daily for 5 days.

Each rat of Group 1 was intramuscularly injected with Lys-Glu-Asp-Ala (SEQ ID NO: 1) tetrapeptide in solution form in the dose of 1 µg for 5 days accompanying $CCl_4$ administration. In 5 days after the tetrapeptide administration completion, the rats were euthanaised and the investigation results were assessed.

Animals of the other group were intramuscularly administered with Lys-Glu-Asp-Ala (SEQ ID NO: 1) tetrapeptide in solution form after the end of $CCl_4$ impact in the dose of 1 µg per injection, daily for 15 days. In 20 days after the experiment onset, the rats were euthanaised.

The control animals received natural saline injections according to the same plans.

The state of the animals' liver was assessed by the data of biochemical analysis defining the concentration of protein, bilirubin, cholesterol, alanine aminotransferase (ALT) and aspartate aminotransferase (AST).

Morphological alterations of the liver were revealed on histology. Tissue bits were fixed in 10% formalin solution in a 0.1M sodium phosphate buffer (pH 7.4). The histological preparations were stained with haematoxylin-eosin, staining for fat was performed with Sudan-3 and for glycogen— according to McManus.

The conducted studies exposed expressed lesions in the liver of the rats in 5 days after $CCl_4$ impact. Decreased content of the total protein, levels of bilirubin and cholesterol were registered. The activity of aminotransferases rose intensely (Table 1).

Post mortem examination exposed the signs of large-drop adipose degeneration (Table 2). In 84.6% of the cases, hepatocytes had inclusions of fat. Signs of plasmolysis accompanying disturbed glycogen synthesis were observed in the hepatocytes. Congestive plethora, haemorrhages, disseminated lymphoid cellular infiltration and oedema of Disse's spaces were noted.

Biochemical and morphological data demonstrated the development of acute toxic hepatitis with the signs of liepatocyte destruction in the animals because of the hepatotropic poisoning.

Simultaneous administration of $CCl_4$ and Lys-Glu-Asp-Ala (SEQ ID NO: 1) tetrapeptide resulted in a less expressed liver destruction, which was evidenced by the biochemical data. The content of total protein and cholesterol and bilirubin concentration in the blood increased. Aminotransferase activity was higher than in the intact animals but lower than in the hepatitis-bearing ones (Table 1).

The liver pathology was less expressed in the rats that received Lys-Glu-Asp-Ala (SEQ ID NO: 1) tetrapeptide during the period of $CCl_4$ impact. Adipose degeneration was registered in 40–50% of the hepatocytes (Table 2). Lymphoid cellular infiltration of the periportal tracts was preserved. Signs of regeneration in the form of solitary binuclear hepatocytes were observed. Forty five percent of the hepatocytes revealed glycogen synthesis.

The adduced data demonstrate that the investigated tetrapeptide restricts the development of liver pathology. It decreases enzyme content in the blood, restricts the signs of hepatocellular deficiency and thrombus-haemorrhage syndrome enlarging the regeneration foci in the liver.

On the $20^{th}$ day of the experiment the biochemical blood indices in the controls revealed a tendency to restoration but did not reach the normal limits (Table 1). Adipose liver degeneration was preserved in 16.7% of the hepatocytes. Regeneration sites accompanied by lymphoid cellular infiltration were registered. Glycogen in the hepatocytes with adipose degeneration was not found, while it was revealed in the other cells in the form of fine granules (Table 2).

The animals treated with the tetrapeptide during 15 days after the end of CCl$_4$ impact had the concentration of protein, bilirubin, cholesterol and aminotransferases in the blood restored to the normal values (Table 1).

TABLE 1

Effect of Lys-Glu-Asp-Ala (SEQ ID NO: 1) tetrapeptide on the biochemical blood indicies in rats with acute toxic hepatitis

| Indices | Intact animals | Day 5 | | Day 20 | |
|---|---|---|---|---|---|
| | | Control | Lys-Glu-Asp-Ala tetrapeptide accompanying CCl$_4$ impact | Control | Lys-Glu-Asp-Ala tetrapeptide after CCl$_4$ impact |
| Protein, g/l | 86.5 ± 4.2 | 64.4 ± 3.1* | 77.8 ± 3.7** | 75.2 ± 2.1* | 83.4 ± 3.4** |
| Total bilirubin, μmole/l | 13.2 ± 1.3 | 6.2 ± 1.2* | 12.5 ± 2.1** | 9.1 ± 1.1* | 14.8 ± 3.2** |
| Cholesterol, mm/l | 4.3 ± 0.3 | 2.7 ± 0.3* | 4.1 ± 0.25** | 3.2 ± 0.3* | 4.2 ± 0.35** |
| ALT, international units per ml | 6.1 ± 1.1 | 53.0 ± 4.2* | 35.3 ± 3.8** | 9.6 ± 1.2* | 5.3 ± 0.98** |
| AST, international unit per ml | 12.8 ± 2.1 | 54.0 ± 5.9* | 35.6 ± 4.3** | 19.2 ± 1.3* | 11.3 ± 1.9** |

*P < 0.05 in comparison with the indices for intact animals;
**P < 0.05 in comparison with the indices for the corresponding control groups.

These rats revealed no signs of degeneration. Hepatocytes had fine-granular plasma and rounded nuclei. Solitary lymphocytes were found in the lobules. The architectonics of the lobules was not damaged. Binuclear hepatocytes with hyperchromised nuclei evidenced regeneration as a typical sign thereof. Fine-granular glycogen was evenly spread throughout the cytoplasm. Staining for fat was negative in 90% of the hepatocytes (Table 2).

TABLE 2

Effect of Lys-Glu-Asp-Ala (SEQ ID NO: 1) tetrapeptide on hepatocytes pathomorphological indices in rats with acute toxic hepatitis

| Indices | Day 5 | | Day 20 | |
|---|---|---|---|---|
| | Control | Lys-Glu-Asp-Ala tetrapeptide accompanying CCl$_4$ impact | Control | Lys-Glu-Asp-Ala tetrapeptide after CCl$_4$ impact |
| Hepatocytes with fat inclusions, % | 84.3 ± 9.2 | 49.8 ± 6.3* | 26.7 ± 3.8 | 10.0 ± 2.1* |
| Hepatocytes with glycogen synthesis, % | 31.6 ± 4.1 | 45.0 ± 4.3 | 70.0 ± 5.3 | 90.0 ± 8.1* |

*P < 0.05 in comparison with indices for the corresponding control groups.

The conducted investigations demonstrate that application of Lys-Glu-Asp-Ala (SEQ ID NO: 1) tetrapeptide in rats with acute toxic hepatitis normalises pigment metabolism, diminishes enzyme content in the blood and decreases the hepatocellular deficiency signs. It spawns regeneration foci in the damaged liver and promotes a faster recovery of the animals.

EXAMPLE 6
Effect of Lys-Glu-Asp-Ala (SEQ ID NO: 1) Tetrapeptide on the Growth of Transplanted Hepatoma-27

The study was performed on 37 female rats weighing 150-200 g with hepatoma-27 subcutaneously transplanted to the right femur region. The experimental animals were subcutaneously injected with 1 μg/kg of Lys-Glu-Asp-Ala (SEQ ID NO: 1) tetrapeptide in solution form, daily for 10 days from the first day after the tumour transplantation. The control animals received natural saline injections by the similar plan. Cyclophosphamide administered once intraperitoneally in the dose of 100 μg/kg was employed as a positive control. The tumour dynamics and animals' survival rate were assessed in experiments.

Figure 3:
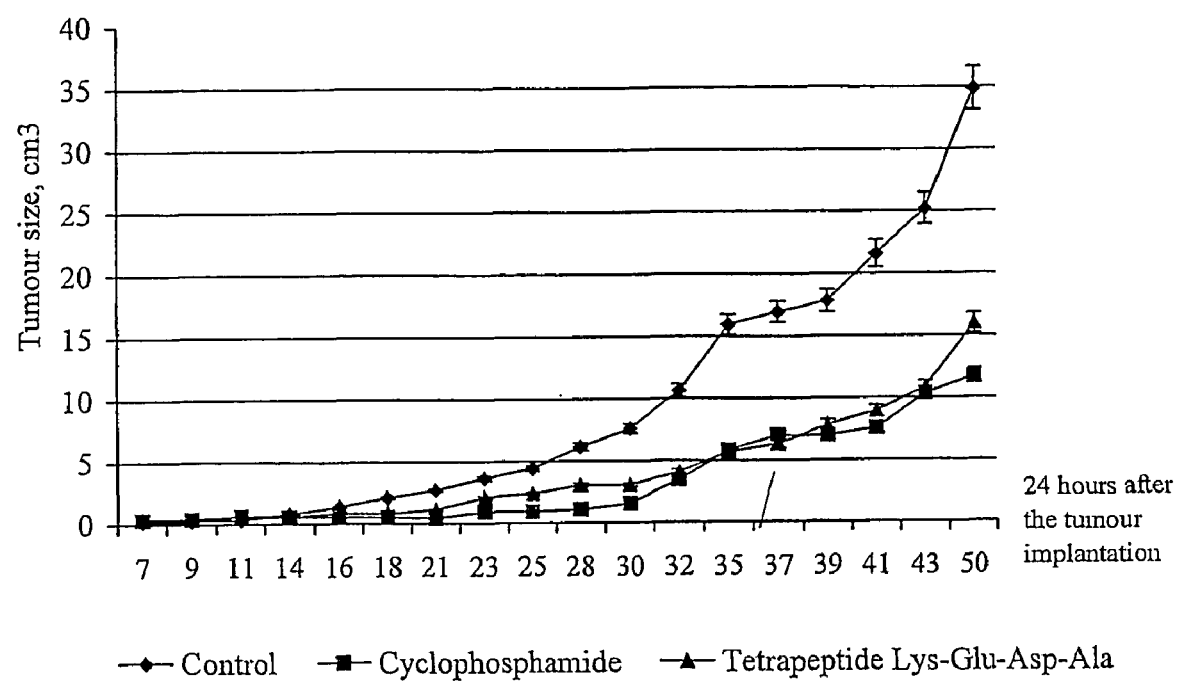

FIG. 3 demonstrates the effect of Lys-Glu-Asp-Ala (SEQ ID NO: 1) tetrapeptide on the growth of hepatoma-27 in rats.

Administration of Lys-Glu-Asp-Ala (SEQ ID NO: 1) tetrapeptide was proven to inhibit the tumour growth at rather late stages of development, though the first signs of hepatoma inhibition were registered already on the 21$^{st}$ day after the transplantation (FIG. 3). However, this effect got stabilised since the 30$^{th}$ day of the experiment. On the 30$^{th}$ day of the experiment, the tumour size in the tetrapeptide-treated animals was 2.5 times less than that in the controls. This effect was preserved up to the end of the data taking on the 50$^{th}$ day of the experiment. Thus, the administration of the liver peptide caused a stable inhibition of the tumour growth. Three animals revealed a complete tumour resolution on the 16$^{th}$, 25$^{th}$ and 43$^{rd}$ days after the tumour transplantation.

Cyclophosphamide application promoted a stable decrease in the tumour growth rate starting from the 16$^{th}$ day after the tumour transplantation (FIG. 3). A complete tumour resolution was registered in three animals of this group on the 28$^{th}$, 32$^{nd}$ and 41$^{st}$ days of the experiment.

At later periods after the transplantation, some part of the tumours started to ulcerate both in the experimental and control animals. Lys-Glu-Asp-Ala (SEQ ID NO: 1) tetrapeptide was stated to affect the incidence and risk of ulceration.

Application of the tetrapeptide from the 39<sup>th</sup> day after the transplantation (when skin ulcers in the tumour lesion site appeared in more than one half of the controls) facilitated a significant decrease in the proportion of ulcer-bearing animals. Cyclophosphamide exerted a similar influence only on the 43<sup>rd</sup> day.

The analysis of the experimental animals' survival rate after hepatoma transplantation showed that Lys-Glu-Asp-Ala (SEQ ID NO: 1) tetrapeptide introduction spawned a tendency to increased longevity (Table 3). Consequently, application of Lys-Glu-Asp-Ala (SEQ ID NO: 1) tetrapeptide inhibited the growth of hepatoma-27, which promoted functional normalisation of the liver, improved the general state of the animals and extended their longevity.

TABLE 3

Effect of Lys-Glu-Asp-Ala (SEQ ID NO: 1) tetrapeptide on the mean life span in rats with hepatoma-27

| Group of animals | Mean life span (days after the tumour transplantation) |
| --- | --- |
| Control | 55.00 ± 6.56 |
| Cyclophosphamide | 61.50 ± 4.58 |
| Lys-Glu-Asp-Ala tetrapeptide | 68.00 ± 1.23 |

EXAMPLE 7

Efficacy of Lys-Glu-Asp-Ala (SEQ ID NO: 1) Tetrapeptide Application in the Patients With Chronic Persistent Hepatitis The trial was carried out on 23 patients aged 32–53 years. The disease duration constituted 10–20 years. 79% of the patients had virus hepatitis A in the case history and 11%—virus hepatitis B. The majority of the patients complained of pains in the right hypochondrium, general weakness and quick fatigability. 45% of the patients noted dyspeptic disorders. All the patients had previously received periodic conventional medications.

Lys-Glu-Asp-Ala (SEQ ID NO: 1) tetrapeptide in solution form was intramuscularly injected once a day in the dose of 0.01–100 µg/kg of the body weight in the course of 10–40 days depending on the disease severity. The control group included 12 analogous patients treated by conventional methods.

The patients' complaints were assessed in dynamics. Performed were total blood and urine counts, biochemical blood investigation ("REFLOTRON", Boehringer Mannheim, Germany) and immune assay of the peripheral blood (definition of Ig according to Mancini). Ultrasound investigation of the liver was carried out on an ultrasound apparatus (ALOKA, Japan). Against the background of the applied treatment 93% of the patients noted weakness elimination, improved appetite and increased workability. 51% of the patients revealed a significantly lower intensity of the pain syndrome. The biochemical test results were in the focus of attention during the patients' examination. They reflected aminotransferase activity, pigment- and protein-forming functions of the liver. 72% of the patients registered hyperbilirubinemia, increased level of alanine aminotransferase (ALT) and slight rise in γ-globulin fraction of the blood proteins, chiefly, due to IgM, which evidenced a certain activity of the chronic inflammatory process. Application of Lys-Glu-Asp-Ala (SEQ ID NO: 1) tetrapeptide facilitated normalisation of bilirubin level and ALT activity (Table 4).

TABLE 4

Effect of Lys-Glu-Asp-Ala (SEQ ID NO: 1) tetrapeptide on the biochemical indices of the peripheral blood in the patients with chronic persistent hepatitis

| Indices (mmole/l) | Before treatment | After treatment |
| --- | --- | --- |
| Cholesterol | 4.9 + 0.5 | 5.1 + 0.3 |
| Bilirubin | 26.3 + 1.8 | 21.7 + 1.5* |
| AST | 39.4 + 3.7 | 38.5 + 2.4 |
| ALT | 53.1 + 4.7 | 40.8 + 3.1* |
| GGT | 44.3 + 3.9 | 41.6 + 4.5 |
| Triglycerides | 2.4 + 0.3 | 2.2 + 0.2 |

*$P < 0.05$ in comparison with the indices before treatment.

Investigation of the peripheral blood immunoglobulins, an essential criterion of the inflammatory process activity, after a course of the tetrapeptide therapy showed a decrease in IgM level (Table 5).

TABLE 5

Effect of Lys-Glu-Asp-Ala (SEQ ID NO: 1) tetrapeptide on the immunological indices in the patients with chronic persistent hepatitis

| Indices (g/l) | Before treatment | After treatment |
| --- | --- | --- |
| IgA | 2.10 + 0.09 | 2.30 + 0.07 |
| IgM | 3.80 + 0.06 | 1.50 + 0.03* |
| IgG | 14.7 + 1.3 | 13.9 + 0.9 |

*$P < 0.05$ in comparison with the indices before treatment.

Thus, the obtained results demonstrate that application of Lys-Glu-Asp-Ala (SEQ ID NO: 1)tetrapeptide in the patients with chronic persistent hepatitis normalises metabolic processes in the liver, decreases the inflammatory process activity and prevents the death of hepatocytes.

REFERENCES

1. Grunnet N., Peng X., Tygstrup N. Growth factors and gene expression in cultured rat hepatocytes.—J. Hepatol.—1999.—Vol. 31,No. 1.—P. 117–122.
2. Imanishi Ji, Kamiyama K., Iguchi I. et al. Growth factors: importance in wound healing and maintenance of transparency of the cornea.—Prog. Retin. Eye Res.—2000.—Vol. 19, No. 1.—P. 113–129.
3. Kaido T., Yoshikawa A., Seto S. et al. Hepatocyte growth factor supply accelerates compensatory hypertrophy caused by portal branch ligation in normal and jaundiced rats.—J. Surg. Res.—1999.—Vol. 85, No. 1.—P. 115–119.
4. Mashkovsky M.D. Pharmaceutical substances (Manual for Physicians).—Part I.—Medicina, Moscow.—1993.—P. 610–615.
5. Mashkovsky M.D. Pharmaceutical substances (Manual for Physicians).—Part II.—Medicina, Moscow.—1993.—P.47–56.
6. Pharmaceutical substances of foreign manufacturers in Russia: Reference Book.—AstraPharmServis, Moscow, 1993.—P. 501–502.
7. Ueki T., Kaneda Y., Tsutsui H. et al. Hepatocyte growth factor gene therapy of liver cirrhosis in rats.—Nat. Med.—1999. —Vol. 5, No. 2. —P. 226–230.
8. Yakubke Kh. -D., Eshkeit Kh. Amino acids, peptides, proteins: Translated from German.—Mir, Moscow. 1985.–456 pp.

The invention claimed is:

1. A tetrapeptide lysyl-glutamyl-aspartyl-alanine of SEQ ID NO: 1.

2. A pharmaceutical composition capable of stimulating the functional activity of hepatocytes and comprising as the active base an effective quantity of tetrapeptide lysyl-glutamyl-aspartyl-alanine of SEQ ID NO: 1 or one of its pharmaceutically admissible salts and a pharmaceutically admissible carrier.

3. A method for treating a disease or pathologic state requiring stimulation of hepatocytic functional activity in a patient comprising administering to the patient a therapeutically effective quantity of tetrapeptide lysyl-glutamyl-aspartyl-alanine of SEQ ID NO: 1 or one of its pharmaceutically admissible salts and a pharmaceutically admissible carrier.

4. The method according to claim 3 wherein one of the salts of the amino group is selected from the group consisting of acetate, hydrochloride and oxalate.

5. The method according to claim 3 wherein one of the salts of carboxyl group is selected from the group consisting of the salts of sodium, potassium, calcium, lithium, zinc, magnesium or from organic and inorganic cations selected from the group consisting of ammonium and triethylammonium.

6. The method according to claim 3 wherein the administration is parenteral administration.

7. The method according to claim 3, wherein the tetrapeptide or a salt thereof is administered in a dose 0.01–100 µg/kg of the body weight at least once a day during a period required for attaining a therapeutic effect.

8. The method of claim 4, wherein the tetrapeptide or a salt thereof is administered in a dose 0.01–100 µg/kg of the body weight at least once a day during a period required for attaining a therapeutic effect.

9. The method of claim 5, wherein the tetrapeptide or a salt thereof is administered in a dose 0.01–100 µg/kg of the body weight at least once a day during a period required for attaining a therapeutic effect.

10. The method of claim 6, wherein the tetrapeptide or a salt thereof is administered in a dose 0.01–100 µg/kg of the body weight at least once a day during a period required for attaining a therapeutic effect.

11. A method of stimulating in a patient functional activities of hepatocytes selected from the group consisting of protein synthesis, cell proliferation, cell migration, cell differentiation, repair ability of damaged liver structures, bilirubin and cholesterin metabolism and glycogen synthesis, comprising administering to the patient a therapeutically effective quantity of tetrapeptide lysyl-glutamyl-aspartyl-alanine of SEQ ID NO: 1 or one of its pharmaceutically admissible salts, and a pharmaceutically acceptable carrier.

* * * * *

UNITED STATES PATENT AND TRADEMARK OFFICE
CERTIFICATE OF CORRECTION

PATENT NO.        : 7,101,854 B2                                        Page 1 of 1
APPLICATION NO.   : 10/398690
DATED             : September 5, 2006
INVENTOR(S)       : Khavinson It is certified that error appears in the above-identified patent and that said Letters Patent is hereby corrected as shown below:

ON THE TITLE PAGE:

Item [30]
In Foreign Application Priority Data, line 1: "2001125353" should read --2000125353--

Signed and Sealed this

Twenty-sixth Day of December, 2006

JON W. DUDAS
*Director of the United States Patent and Trademark Office*